United States Patent [19]

Polski

[11] Patent Number: 5,004,630
[45] Date of Patent: Apr. 2, 1991

[54] PROCESS OF MAKING ZONE ADHESIVE/RELEASE COATED TAPE

[75] Inventor: Stephen P. Polski, St. Paul, Minn.

[73] Assignee: Minnesota Mining and Manufacturing Company, St. Paul, Minn.

[21] Appl. No.: 520,535

[22] Filed: May 8, 1990

[51] Int. Cl.$^5$ .............................................. B05D 5/10
[52] U.S. Cl. ..................... 427/208.8; 427/336; 427/411; 427/412.1; 427/412.3; 427/412.5
[58] Field of Search ................. 427/208.8, 336, 411, 427/412.1, 412.3, 412.5

[56] References Cited

U.S. PATENT DOCUMENTS

| | | | |
|---|---|---|---|
| 2,532,011 | 11/1950 | Dahlquist et al. | 154/53.5 |
| 3,853,129 | 12/1974 | Kozak | 128/287 |
| 3,862,634 | 1/1975 | Small | 128/284 |
| 3,874,386 | 4/1975 | Kozak | 128/287 |
| 3,930,502 | 1/1976 | Tritsch | 128/287 |
| 3,937,221 | 2/1976 | Tritsch | 128/287 |
| 3,950,824 | 4/1976 | Karami | 24/67 AR |
| 3,970,086 | 7/1976 | Cheslow | 128/287 |
| 3,985,136 | 10/1976 | Cepuritis | 128/287 |
| 3,987,793 | 10/1976 | Milnamow | 128/287 |
| 3,999,544 | 12/1976 | Feldman et al. | 128/284 |
| 3,999,545 | 12/1976 | Milnamow | 128/284 |
| 4,050,121 | 9/1977 | Richman | 24/73 VA |
| 4,084,592 | 4/1978 | Tritsch | 128/287 |
| 4,097,627 | 6/1978 | Nemeth et al. | 428/40 |
| 4,144,887 | 3/1979 | Milnamow | 128/287 |
| 4,177,812 | 12/1979 | Brown et al. | 128/284 |
| 4,237,890 | 12/1980 | Laplanche | 128/287 |
| 4,568,344 | 2/1986 | Suzuki et al. | 604/389 |
| 4,576,598 | 3/1986 | Tritsch | 604/390 |
| 4,576,600 | 3/1986 | Joa | 604/390 |
| 4,670,012 | 6/1987 | Johnson | 604/390 |
| 4,886,680 | 12/1989 | Tindall | 427/8 |

FOREIGN PATENT DOCUMENTS

3440544A1 5/1986 Fed. Rep. of Germany .
2151460A 7/1985 United Kingdom .

Primary Examiner—Bernard Pianalto
Attorney, Agent, or Firm—Gary L. Griswold; Roger R. Tamte; William J. Bond

[57] ABSTRACT

There is provided an adhesive closure tab with release surfaces adjacent adhesive surfaces by coating a continuous region of a tape backing with a soluble low adhesion backsize composition, drying, then solvent zone coating an adhesive on at least one strip of said tape backing previously coated with the low adhesion backsize thereby slightly dissolving said backsize so as to promote adherence of said adhesive to said backsize.

7 Claims, 1 Drawing Sheet

PROCESS OF MAKING ZONE ADHESIVE/RELEASE COATED TAPE

This invention relates to a pressure-sensitive adhesive fastening tape or tab for use in garment closures and the like. Particularly, the invention relates to adhesive fastening tabs for use in disposable garments such as diapers having a fastening surface which when not in use are placed against a release coated surface.

BACKGROUND AND FIELD OF THE INVENTION

Disposable garments, principally disposable diapers, extensively utilize adhesive fastening tabs to effect closure of the garment. Adhesive fastening tabs have gained widespread popularity due to their versatility, cost, and advantages over older conventional type fasteners, such as safety pins, snaps or zippers.

A typical commercial adhesive fastening tab has two separate attachment ends, one end permanently attached to the garment and one "free" end placed by the user. The user placed end allows for adjustablity. However, this user-placed, adhesive attachment end of the fastening tab generally causes placement problems prior to its use. The free adhesive end must be conveniently and removably stored in a manner such that the adhesive is functional and available for use for a significant period of time after manufacture. This is conventionally done by protecting the adhesive surface of the free attachment end by adhering it to a release composition (e.g., a low surface energy polymer) coated tape.

The release coated tape can be a separate tape which covers the free adhesive end of the fastening tab prior to use. When the user wishes to place the free end of the fastening tab, the release tape is peeled away and discarded exposing the free adhesive end for closure. Examples of this approach are discussed in U.S. Pat. Nos. 3,930,502 (Tritsch), 3,970,086 (Cheslow) and 4,576,598 (Tritsch) (who uses a release coated tape which has release coating on both faces). A problem with this approach however is the need to separately dispose of the release tapes.

Another approach has been to locate the release tapes on the diaper itself at a location suitable for attaching the free end or portion of the fastening tab, yet at a place that will not interfere with attachment of the free end when the fastening tab is used. Examples of this approach are discussed in U.S. Pat. Nos. 3,985,136 (Cepuritis) (located on inner diaper face), 3,987,793 (Milnamow) (same), 3,999,545 (Milnamow) and 4,144,887 (Milnamow). This approach is advantageous in that it doesn't require a separate release tape or separate disposal of the release tape, but it is often complex in manufacture and construction.

The third main approach has been to make the release tape integral with the fastening tab. In this approach the fastening tab is folded in a manner which permits the free adhesive end of the fastening tab to be in contact with a separate portion of the same tab where a release coated surface is located. The most common method for placing a release coating on the fastening tab is to zone coat a release coating directly onto the fastening tab substrate as per U.S. Pat. Nos. 3,999,544 (Feldman et al.), 4,084,592 (Tritsch), 3,862,634 (Small), 3,950,824 (Karami), 4,050,121 and 4,097,627 (Nemeth et al.). The adhesive is also separately zone coated directly onto the fastening tab in these patents. Very often a zone coated adhesive strip is directly adjacent to a zone coated release strip. This can cause significant manufacturing problems due to the incompatible nature of release and adhesive coatings, making it difficult to coat them side by side simultaneously. For example, if the release and adhesive coatings are sequentially applied, overlapping the two strips typically causes incompatibility related problems, making the product difficult to collect as a roll.

It has also been proposed to release coat one entire side of a film which is then placed, non-coated side down, as a strip on a portion of a tape that has a full coating of adhesive, U.S. Pat. No. 4,177,812 (Brown et al). This approach allows one to readily locate a release coated surface directly adjacent to an adhesive coated surface but at a significantly greater cost in materials and handling.

Other approaches include those discussed in U.S. Pat. No. 4,237,890 (Laplanche), which discloses a fastening tab where a separate release coated strip is attached directly to the fastening tab using a narrow strip of glue separate from the pressure-sensitive adhesive on the tab; U.S. Pat. No. 3,853,129 (Kozak), which discloses using a retiform surface that serves as a release layer (i.e., by providing a low adhesive contact area), and U.S. Pat. No. 4,670,012 (Johnson) which proposes eliminating a release surface by using an adhesive with a low peel force. These approaches are generally not desirable from a manufacturing, cost and/or performance perspective.

SUMMARY OF THE INVENTION

The invention is directed to a simple and inexpensive method for forming a tape or fastening tab having a release surface thereon directly adjacent to an adhesive surface. This tape or tab is ideally suited for use as a diaper, or other disposable garment, closure which is formed prior to, or sequential with, assembly of the diaper garment. For example, the tape can be wound into roll form with a conventional low adhesion backsize coating, and then cut into closures immediately prior to assembly.

The tape is formed by coating a release composition onto a substrate. The release coated layer is then permitted to at least partially dry followed by zone coating adhesive on the same face of the tape substrate. The adhesive is applied in a solvent able to partially dissolve the release coating. This allows at least partial softening of the release layer and bonding of the release layer to the adhesive layer. This method permits formation of adhesive and release coatings side by side with clean edges using conventional unregistered zone coaters.

DETAILED DESCRIPTION OF THE PREFERRED EMBODIMENTS

Figure 1:
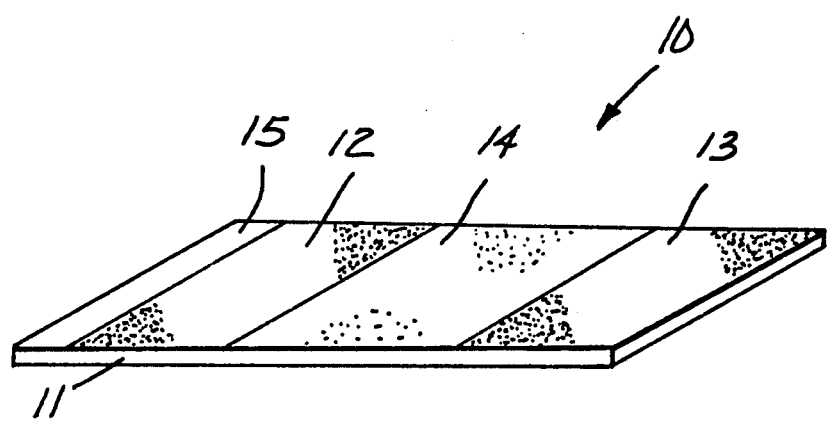
FIG. 1 is a schematic of a diaper fastening tab which can be formed in accordance with the invention process.

The fastening tab of the invention could be of a construction such as that shown in FIG. 1. Fastening tab 10 is provided with adhesive strips 12 and 13. Adhesive strip 13 could be used to attach the fastening tab to the diaper, preferably at a corner of the diaper outer shell (the outer surface of the diaper, typically a polyolefin impervious to liquid), and could be a conventional pressure-sensitive adhesive, (PSA). However, adhesive 13 could be omitted and the fastening tab 10 adhered to the diaper by other conventional methods, such as by sonic welding. Adhesive strip 12 is also preferably a PSA and is located on the free end of the fastening tab. Prior to using the fastening tab 10, the portion of the fastening tab 10 having the strip of adhesive 12 would be folded over onto the release coated area 14. Optional end portion 15 of the tab could be uncoated or provided with a release coating as needed and is used to facilitate gripping of the tab by the user.

According to the invention process, a fastening tab such as tab 10 in FIG. 1 would be produced by coating a conventional substrate 11 with a suitable release agent. The substrate could be any susceptible to coating with a release coating contemplated by the invention which includes polyolefin films such as those of polyethylene or polypropylene, polyesters, polyvinylchloride(PVC), glassine paper, or the like.

The release coating 14 applied to the substrate can be any which will adequately bond to a later applied solvent coated adhesive. Generally, curable release coatings such as many of the silicone-based release agents are unacceptable. However, many, if not most, solvent-coated release agents will work if used with the proper adhesive coating solution. Solvent-based release agents include, for example, acrylic polymers, urethanes or polycarbamates, certain fluoro chemicals, e.g., perfluoropolyether based backsides, imides, amides, and imines. Preferred are the polyvinyl alkyl carbamate release agents such as polyvinyl octadecyl carbamate disclosed in U.S. Pat. No. 2,532,011 (Dahlquist et al), the substance of which is hereby incorporated by reference. These release agents are preferably solvent coated using suitable conventional solvents such as methyl ethyl ketone, heptane, aromatic hydrocarbons such as xylene, benzene or toluene, tetrahydrofuran, butyl acetate, dioxane or admixtures thereof.

The release coating 14 can be coated onto an entire substrate surface or on only selected zones thereof. It is preferred in terms of manufacturing simplicity and product uniformity that the release agent be coated over an entire substrate face that is to be later solvent coated with adhesive.

After coating, the release agent is allowed to dry, preferably for 2 to 5 seconds. Any curing, if required or desired, of the release agent should be avoided prior to coating with the adhesive solution. Curing could render the dried release agent insoluble to later applied solvents or solutions.

After drying, the release coated substrate is adhesive zone coated with, preferably, a conventional zone coater. Any suitable solvent based adhesive composition is generally acceptable for use in the invention process, including adhesives based on natural or synthetic rubber, acrylic polymers, vinyl ether polymers or the like. These adhesives must be in a solvent system which will partially dissolve a portion of the release coating previously applied. Any conventional solvent or solvent system, as discussed above, can be used.

The adhesive system zone coated onto the substrate previously coated with release agent should be matched with the particular release coating used. Specifically, the adhesive should be one which will release from the particular release coated surface without blocking. A release coating that will tend to form bonds with a particular adhesive will increase the adherence of the later solvent coated adhesive to the substrate. However, a problem with such a release coating is that the uncoated portion of the release coating 14 would not adequately release the adhesive tab free end 12 when it is folded over onto release coat 14. For example, block copolymer, synthetic rubber-based adhesives are generally not suited for use with acrylate- or fluoro chemical-based release coatings due to a tendency to block on these coatings. Particular adhesives which will adequately release from particular release coatings are known in the art.

Tape constructions other than that of FIG. 1 are contemplated as suitable for manufacture with the invention process. For example, the release coating could be applied to both faces of the substrate to form closure systems such as those disclosed in U.S. Pat. Nos. 4,097,627, 4,050,121, or 4,084,592, discussed above. All these closures and any other design which uses adhesive and release coatings side by side on the same fastening tab or tape would benefit from the invention process.

For constructions where adhesive is used on only one face of the fastening tape or tab, or where adhesive and release layers are spaced apart on a fastening tab or tape, other conventional low adhesion backsizes or release agents can be used in conjunction with the invention process. For example, for a fastening tab like that depicted in FIG. 1, the hidden face has no adhesive. If it would be desirable to form the tape as a roll, from which the fastening tabs are cut, the hidden face could be coated with any conventional backsize or release agent, such as a curable silicone.

EXAMPLE 1

A 4.0 mil (0.10 mm) matte/smooth polypropylene backing was coated full width on the rough (matte) side with Dow Corning(Midland, Mich.) Syloff ™ 294 silicone release system and cured. The smooth side was full width coated with a heptane solution (5% solids) of polyvinyl octadecyl carbamate release agent described in U.S. Pat. No. 2,532,011 and dried. The polyvinyl octadecyl carbamate side was then coated with 2 inch (5.08 cm) strips of solvent (heptane/toluene, 20/80 solution, 55% solids) based tackified styrene/isoprene/styrene (Kraton ™ 1111) adhesive St. Paul, Minn. ), with the strips 1⅛ inch (2.9 cm) apart. The solvent in the adhesive partially dissolved the polyvinyl octadecyl carbamate coating allowing for adequate anchorage of the adhesive layer to the release coated backing after drying.

A 1 inch (2.54 cm) wide tape sample was tested for 90° peel. One adhesive coated end was masked with paper. On the opposite adhesive end, a paper leader was attached on the last ⅛ inch (0.32 cm) to attach to an Instron ™ (Instron Corp., Canton, Mass.) adhesion tester. The back of the tape was covered with a silicone tape to permit adhesion to the steel plate. The free adhesive end was folded over onto the center exposed polyvinyl octadecyl carbamate zone, and the tape was attached to a steel plate with double-coated tape. The tape was given two passes (one in each direction) with a 4.5 lb (2.0 Kg) roller at 12 ft/min (30.5 cm/min). The paper leader was placed in the jaws of the Instron, which was operated at a crosshead speed of 12 in (30.5 cm)/min to yield a 90° peel of 368 gm/in (3.8 N/25 mm).

A second sample was aged for 20 hours in a 120° F. (49° C.) oven and tested in the manner described above yielding a 90° peel of 411 gm/in (4.2 N/25 mm).

The sample was also tested by hand against the frontal tape of a Luvs ™ brand diaper. The tape adhered to the frontal tape and exhibited no adhesive transfer when removed, either immediately or after approximately one week.

Other embodiments of the invention will be apparent to those skilled in the art from a consideration of this specification or practice of the invention disclosed herein. It is intended that the specification and examples be considered as exemplary only with the true scope and spirit of the invention being indicated by the following claims.

I claim:

1. A process for forming an adhesive closure tab with release surfaces adjacent adhesive surfaces comprising the steps of, coating a continuous region of a tape backing with a soluble low adhesion backsize composition, drying said low adhesion backsize composition, solvent zone coating an adhesive on at least one strip of said tape backing previously coated with said low adhesion backsize thereby slightly dissolving said backsize so as to promote adherence of said adhesive to said backsize.

2. The process of claim 1 wherein said soluble low adhesion backsize is applied as an urethane solution.

3. The process of claim 2 wherein said adhesive is applied in a solution.

4. The process of claim 2 wherein said adhesive is applied as an emulsion.

5. The process of claim 2 wherein said adhesive is a natural or synthetic rubber-based composition.

6. The process of claim 2 wherein said adhesive is an acrylate-based adhesive composition.

7. The process of claim 2 wherein said urethane and said adhesive compositions are applied in an organic solution.

* * * * *

UNITED STATES PATENT AND TRADEMARK OFFICE
CERTIFICATE OF CORRECTION

PATENT NO. : 5,004,630

DATED : April 2, 1991

INVENTOR(S) : Stephen P. Polski

It is certified that error appears in the above-identified patent and that said Letters Patent is hereby corrected as shown below:

Column 4, line 42, after the word "adhesive" insert --(available on KR 0269 fastening tape sold by 3M Company,--.

Signed and Sealed this

First Day of December, 1992

*Attest:*

DOUGLAS B. COMER

*Attesting Officer*     *Acting Commissioner of Patents and Trademarks*